United States Patent
Layton

(10) Patent No.: US 6,544,427 B2
(45) Date of Patent: Apr. 8, 2003

(54) CLEAN WATER FOR DENTAL DELIVERY UNITS

(76) Inventor: Grant H. Layton, 3448 Camino Alegre, Carlsbad, CA (US) 92008

( * ) Notice: Subject to any disclaimer, the term of this patent is extended or adjusted under 35 U.S.C. 154(b) by 36 days.

(21) Appl. No.: 09/792,339

(22) Filed: Feb. 26, 2001

(65) Prior Publication Data

US 2002/0148789 A1 Oct. 17, 2002

(51) Int. Cl.$^7$ .................................................. C02F 1/50
(52) U.S. Cl. .................. 210/764; 422/28; 422/186; 205/742; 252/175
(58) Field of Search ................ 210/764; 422/28, 422/186; 205/742; 252/175

(56) References Cited

U.S. PATENT DOCUMENTS 4,545,956 A * 10/1985 Ciszewski et al.
6,214,299 B1 * 4/2001 Holladay et al.
6,276,895 B1 * 7/2001 Engelhard et al.

* cited by examiner

Primary Examiner—Betsey Morrison Hoey
(74) Attorney, Agent, or Firm—Clayton, Howarth & Cannon, P.C.

(57) ABSTRACT

A method of producing Clean Water for Dental Delivery Units is described using colloidal silver to sanitize the water supply of dental water delivery units. The silver compound is generated by means of a proprietary process contained in a U.S. patent application. The Clean Water for Dental Delivery Units method is capable of delivering sterile water to dental patients from existing equipment with complete safety for patients and dental office staff.

26 Claims, 1 Drawing Sheet

CLEAN WATER FOR DENTAL DELIVERY UNITS

FIELD OF THE INVENTION

The present invention relates generally to dental equipment hygiene. More specifically, the present invention pertains to the employment of colloidal silver as a bactericide for water storage and delivery equipment used in dental offices.

The present invention is particularly useful for safely preventing microbial growth in dental delivery unit water lines. Microbial growth in dental water delivery lines has been identified as a significant problem.

Methods have been devised and are being sold to sanitize the lines. They are all subject to failure. Mechanisms can fail and allow bacteria to grow, and bacteria grows back between chemical flush sanitations, and where filters are used, bacteria grows back between the filter and the outflow.

Current sanitization technologies include purging and flushing systems, and protocols, back-flow preventers, ultra-violet water purifiers, heat sterilization of lines and units, and water filtration with sub-micron particulate filters.

To date, there have been several patents claiming uses for a multi-valent silver colloid produced by chemical or electrolytic means. U.S. Pat. No. 5,223,149 in particular describes the use of tri-valent silver colloid generated by chemical means, such as reacting Ag(III) tetrasilver trioxide with a ligand bearing compound capable of forming Ag(III) complexes, or other chemical means. U.S. Pat. No. 5,017,295 describes a multivalent silver bactericide used in swimming pools. The present invention uses a colloidal silver solution created by electrolytic means, in a process applied for in U.S. patent application Ser. No. 09/323,310, filed Jun. 1, 1999.

The present invention constitutes a substantial improvement in water hygiene technology for dental offices, over the existing technologies listed above.

BACKGROUND OF THE INVENTION

Microbial growth in water delivery lines is a persistent problem in the dental environment. Typically, dental water delivery units contain small-diameter water supply tubings that carry water to rinse the patient's mouth during dental procedures. Because their inside diameters are approximately 1 millimeter and are made of flexible silicone or other plastic, these water tubings are excellent environments for the development of microbial biofilms. The biofilms shed into the water supply, pose a health risk to dental patients and the office staff, and the microflora also cause foul odor and bad taste in the water. The water containing the bacterial growth is typically sprayed into the patients mouth during dental procedures and the aerosol can be inhaled as well as contacting broken skin.

In light of the above, there is a need for a clean water system for dental office equipment. Accordingly, it is an object of the present invention to provide a dedicated water system for dental office equipment that is essentially sterile. A dedicated water supply in this instance means water from a pressurized canister, not tap water.

It is another object of the present invention to provide the cleanest water system for dental water delivery units which is low-cost and easy to install and maintain.

It is another object of the present invention to use the antimicrobial medium that has the least possibility of deleterious interaction with patient or dental equipment.

It is another object of this invention to eliminate the need for and use of inline microbial filters to eliminate bacteria in the water, and periodic chemical flushes, autoclaving or drying of the lines to remove biofilm that grows on the inside of the water lines.

It is another object of this invention to provide a product that will be shelf stable.

It is a further object of this invention to permit warming the water while discouraging the growth of pathogenic organisms in dental water lines.

It is a further object of this invention to provide a solution that gradually coats the lining of dental water unit tubing with silver and thereby further discourages the growth of microbial colonies.

It is another object of this invention to improve the cleanliness of the vacuum system, vacuum traps and sewers in dentists' offices.

It is another object of this invention to provide water that has no taste or smell.

It is a further object of this invention to achieve the above objects of this invention without requiring changes to dental office water delivery hardware.

SUMMARY OF THE INVENTION

In accordance with the present invention, Clean Water for Dental Delivery Units, dental patient and office staff health and safety will be assured by the addition of colloidal silver to the dedicated water supply of dental delivery units. The Clean Water for Dental Delivery Units invention may be used to safely treat the water supply of dental delivery units to reduce bacterial growth within said water supply.

The Center for Disease Control (CDC) and the American Dental Association (ADA) have called for manufacturers of dental equipment to provide dental delivery units that will deliver water at less than 200 colony forming units (CFU's), measured by bacterial growth on a culture plate. There are existing methods to sanitize Dental Unit Water Lines (DUWLs); they are all subject to failure. Mechanical means can fail and allow bacterial growth, and bacteria will grow past filters and back up the waterlines from point of exit.

The US EPA has established an RfD (Reference Dose) for silver of 0.005 mg/kg of body weight/day. The Reference Dose is the amount that the most sensitive individuals may ingest every day over a 70 year lifetime without likelihood of harm. A 70 kg (154 lb) patient may ingest 0.350 mg of silver each day without exceeding the RfD. This is equivalent to 35 ml of the Ag3p concentrate, or 700 ml of the treated water. In a study done in 1999, rats given a dose of the Ag3p concentrate equal to 11 g/kg of body weight suffered no ill effects (the equivalent dose in a 70 kg human would be 770 ml of the concentrate, or 15.4 liters of treated water). In a 1968 study cited by the EPA, under controlled conditions researchers caused rats to ingest silver at 28,000 times the RfD (140 mg/kg/day) and reported that it was "well tolerated". The EPA does not currently have a drinking water standard for silver. It does publish a secondary (non-enforceable) standard of 0.1 mg/liter based on the RfD. When diluted 20:1 as directed, the Ag3p treated water delivered to the patient will contain silver at 0.5 mg/liter. A typical dental patient will be S exposed to 50–200 ml of this water on each visit, with almost all of this being suctioned away before it can be ingested. If the dentist uses 200 ml of water on a patient, and the patient swallows 10% of it, or 20 ml, that patient will have ingested only 0.010 mg of silver.

This is a negligible amount compared to even the very conservative RfD.

The Clean Water for Dental Delivery Units will be immediately applicable to existing DUWLs in all dental offices without retrofitting of said lines. The present invention can be applied to either de-ionized tap water or distilled water with the same beneficial effect.

The silver solution of this invention is simple and cannot fail because it is simply added to the water in a dedicated water supply system. It is non-toxic, with no taste, and provides pure water that is basically sterile.

As an added bonus, the downstream sewer is cleaner. What used to be a foul, stinking job of cleaning the "trap" below a dental unit is now a relatively clean experience. This means that the vacuum lines are also free of bacteria.

The colloidal silver used by this invention is created by a proprietary, high-voltage electrolytic process as opposed to the current state of the art, which involves either chemical production or low-voltage production.

Said colloidal silver used in this invention was evaluated by the inventor as to its anti-microbial capabilities. The results of these evaluations are shown in Tables 1, 2, and 3. Note: TNTC in tables below is defined as "Too Numerous To Count"

TABLE 1

Bactericidal and Bacteristatic Effect of Ag3p on Contaminated Dental Unit Water Effluent

| Ag3p Treatment | Test Date | CFU/ml |
| --- | --- | --- |
| Pre-Treatment | Jan. 31, 2000 | 15,200 |
| Treatment Initiated | Feb. 15, 2000 | |
| 10 ppm | Feb. 16, 2000 | 0 |
| 1 ppm | Feb. 25, 2000 | 0 |
| 0.5 ppm | Mar. 23, 2000 | 0 |
| 0.5 ppm | May 11, 2000 | 0 |
| 0.1 ppm | June 14, 2000 | 0 |

TABLE 2

Maintain Dental Unit Effluent Sterility by 0.25 ppm Ag3p

| Ag3p Treatment | Test Date | CFU/ml |
| --- | --- | --- |
| Pre-treatment | Apr. 29, 2000 | TNTC |
| Treatment Initiated | May 7, 2000 | |
| 2 ppm | May 8, 2000 | TNTC |
| 1 ppm | May 9, 2000 | 0 |
| 0.5 ppm | May 11, 2000 | 0 |
| 0.25 ppm | June 14, 2000 | 0 |

TABLE 3

Induction of Dental Unit Sterility by 0.25 ppm Ag3p

| Ag3p Treatment | Test Date | CFU/ml |
| --- | --- | --- |
| Pre-Treatment | June 5, 2000 | TNTC |
| Treatment Initiated | June 5, 2000 | |
| 0.25 ppm | June 6, 2000 | TNTC |
| 0.25 ppm | June 7, 2000 | 1610 |
| 0.25 ppm | June 8, 2000 | 81 |
| 0.25 ppm | June 12, 2000 | 160 |
| 0.25 ppm | June 13, 2000 | 8 |
| 0.25 ppm | June 14, 2000 | 10 |
| 0.25 ppm | June 21, 2000 | 2 |
| 0.25 ppm | June 22, 2000 | 16 |

Table 1 illustrates that treating effluent dental water with 10 ppm of Ag3p initially brought the Colony Forming Units per milliliter (CFU/ml) of bacteria count down from 15,200 to 0 (zero) in one day. The maintenance levels of 1.0 and then 0.5 ppm of Ag3p kept the water sterile. A level of 0.1 ppm was not sufficient to maintain dental water sterility.

Table 2 shows that after treating effluent dental water with initially 2 ppm for one day, then 1 ppm of Ag3p on the second day, water was made sterile. Effluent water was kept sterile for one month by maintaining a 0.25 ppm level of Ag3p, once the CFU/m count had been brought down to 0 (zero).

Table 3. shows that introducing a level of 0.25 ppm of Ag3p into dental effluent water would drastically reduce but not completely eliminate bacteria CFU's. Bacteria were never eliminated from the lines completely, indicating that 0.25 ppm Ag3p was sufficient to maintain but not to achieve sterility, defined as 0 CFU/ml.

As a consequence of these tests, the colloidal solution is being registered with the EPA, which has accepted it for evaluation. Test results by the inventor have shown that the solution eliminates all microbial growth in dental equipment at concentrations of 0.5 ppm and at as low as 0.25 ppm.

EPA tests have shown that the solution is safe for human consumption at much higher concentrations than those that patients would be exposed to in a dental office. The proprietary silver solution is light stable, non-staining, and does not interact with dental equipment.

DESCRIPTION OF THE PREFERRED EMBODIMENT

Figure 1:
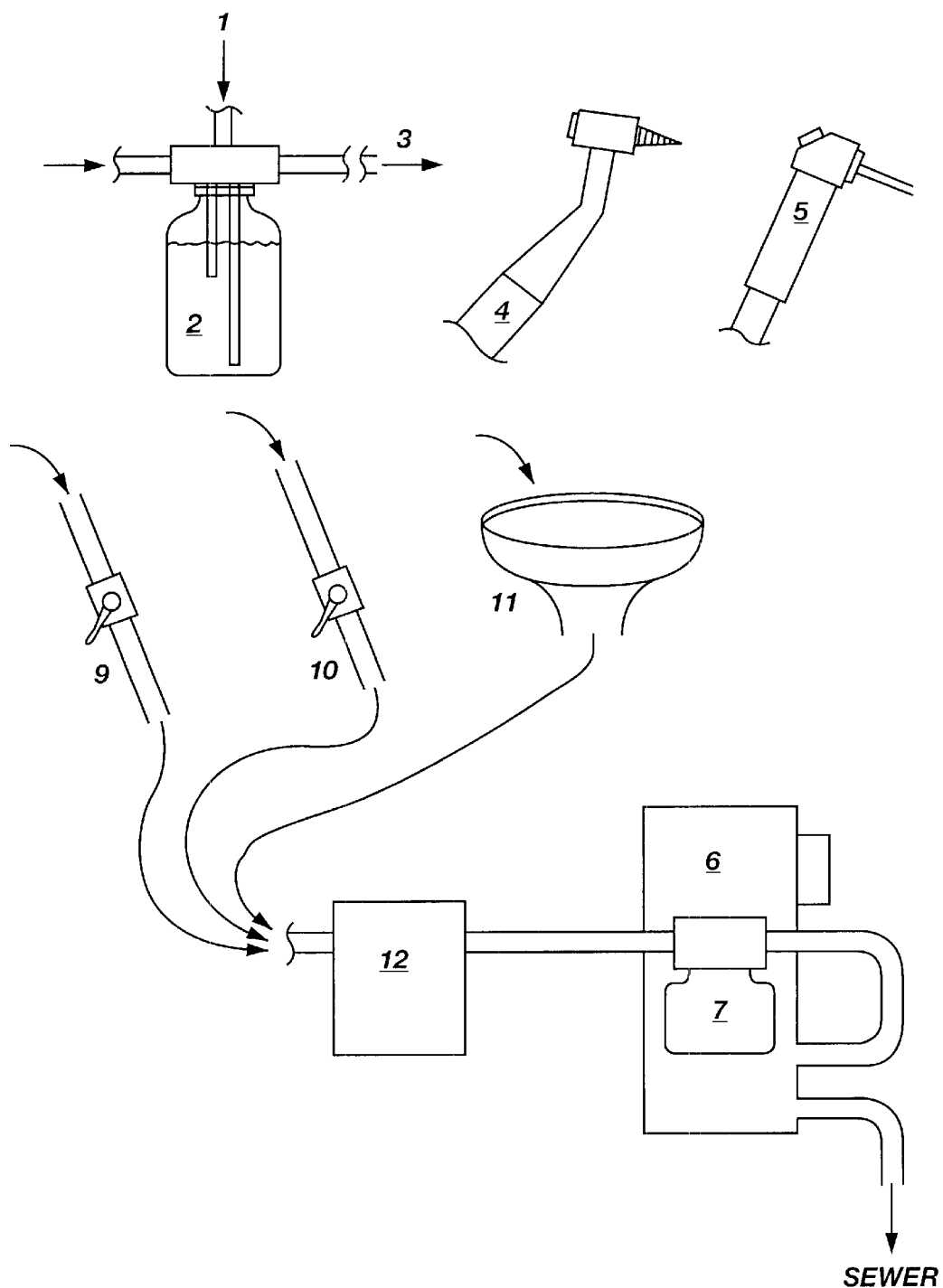
FIG. 1 shows a typical arrangement of dental office water lines, vacuum systems, and sewers.

The silver colloid produced by a Patent Pending method of manufacture consists of minute, uniformly colloid sized (median diameter less than 0.01 micron) particles of metallic silver. Most of these silver particles are coated with various silver oxides, including multi-valent oxides. In addition to helping the product to be extremely shelf stable, these oxides allow the formation of small numbers of multi-valent silver ions ($Ag+2$ and $Ag+3$) which are many times more effective at killing microbes than $Ag+1$ ions.

It is recommended that the colloid be diluted with distilled or de-ionized water. Distilled water is easily and inexpensively purchased locally, or it may be produced by a small in-office distiller. It provides a consistent quality and keeps the dental unit clean and free from contamination.

The subject solution is designed to be used with a closed (bottle type) dental water delivery system. Each time the bottle is refilled, a specific amount of the silver solution is added.

Referring to FIG. 1, a typical closed dental water system has a input for pressurized air 1, a water bottle 2, and a pressurized water output 3 that leads to both the dental drill 4 and syringe 5. The silver treated water is added to the water bottle 2 as needed and supplies the illustrated devices. Used water is accumulated by the high-volume vacuum 9 and low-volume vacuum 10 and at the cuspidor 11. The accumulated water is passed through the vacuum line 8 by pressure from the vacuum 6, through the vacuum trap 12 and filter 7. The water ends up in the dental water sewer.

While the Clean Water for Dental Delivery Units of the present invention as herein shown and disclosed in detail is fully capable of obtaining and providing the advantages herein before stated, it is to be understood that it is merely illustrative of a preferred embodiment of the invention and that no limitations are intended to the details of construction or design herein shown other than as described in the appended claims.

What is claimed is:

1. A method for limiting the growth of microbial films in the water delivery lines of dental offices which comprises the steps of generating a stable silver solution and then adding a specified amount of said solution to water in dental office water reservoirs.

2. The method as claimed in claim 1 where said stable silver solution is generated by electrolytic means.

3. The method as claimed in claim 2 where no inline microbial filters are used in said water delivery lines to eliminate bacteria.

4. The method as claimed in claim 2 where no periodic chemical flushes are used in said water delivery lines.

5. The method as claimed in claim 2 where said stable silver solution will not stain skin or surfaces with which it comes in contact.

6. The method as claimed in claim 2 where said stable silver solution is light stable and shelf-life stable.

7. The method as claimed in claim 2 where said water delivery lines are neither autoclaved nor dried before or after use.

8. The method as claimed in claim 2 where the lumens of said water delivery lines are coated by said stable silver solution, and microbial colonization is thereby further inhibited.

9. The method as claimed in claim 2 where the water in said water delivery lines can be heated without increasing microbial colony counts.

10. The method as claimed in claim 2 where bacterial growth in the downstream vacuum system of dental units, including hoses, traps, and valves is eliminated.

11. The method as claimed in claim 2 where the water in said dental delivery lines is non-toxic, has no taste, and has no smell.

12. The method as claimed in claim 2 where no changes are required to existing dental office water delivery hardware.

13. The method as claimed in claim 2 where the water in said dental delivery units can remain stagnant without becoming foul smelling or bad tasting due to bacterial growth.

14. The method as claimed in claim 1 where said stable silver solution is a solution of multivalent silver.

15. The method as claimed in claim 14 where said stable silver solution is generated by electrolytic means.

16. The method as claimed in claim 15 where no inline microbial filters are used in said water delivery lines to eliminate bacteria.

17. The method as claimed in claim 15 where no periodic chemical flushes are used in said water delivery lines.

18. The method as claimed in claim 15 where said stable silver solution will not stain skin or surfaces with which it comes in contact.

19. The method as claimed in claim 15 where said stable silver solution is light stable and shelf-life stable.

20. The method as claimed in claim 15 where said water delivery lines are neither autoclaved nor dried before or after use.

21. The method as claimed in claim 15 where the lumens of said water delivery lines are coated by said stable silver solution, and microbial colonization is thereby further inhibited.

22. The method as claimed in claim 15 where the water in said water delivery lines can be heated without increasing microbial colony counts.

23. The method as claimed in claim 15 where bacterial growth in the downstream vacuum system of dental units, including hoses, traps, and valves is eliminated.

24. The method as claimed in claim 15 where the water in said dental delivery lines is non-toxic, has no taste, and has no smell.

25. The method as claimed in claim 15 where no changes are required to existing dental office water delivery hardware.

26. The method as claimed in claim 15 where the water in said dental delivery units can remain stagnant without becoming foul smelling or bad tasting due to bacterial growth.

* * * * *